United States Patent
Yamanari

(10) Patent No.: US 9,995,565 B2
(45) Date of Patent: Jun. 12, 2018

(54) OPTICAL COHERENCE TOMOGRAPHY USING POLARIZATION INFORMATION

(71) Applicant: Tomey Corporation, Nagoya-shi (JP)

(72) Inventor: Masahiro Yamanari, Nagoya (JP)

(73) Assignee: TOMEY CORPORATION, Nagoya-Shi (JP)

( * ) Notice: Subject to any disclaimer, the term of this patent is extended or adjusted under 35 U.S.C. 154(b) by 154 days.

(21) Appl. No.: 15/134,828

(22) Filed: Apr. 21, 2016

(65) Prior Publication Data

US 2016/0313112 A1    Oct. 27, 2016

(30) Foreign Application Priority Data

Apr. 23, 2015    (JP) .................................. 2015-088041

(51) Int. Cl.
| | |
|---|---|
| G06K 9/00 | (2006.01) |
| G01B 9/02 | (2006.01) |
| A61B 3/10 | (2006.01) |
| A61B 5/00 | (2006.01) |
| A61B 3/00 | (2006.01) |

(52) U.S. Cl.
CPC ........ *G01B 9/02083* (2013.01); *A61B 3/0025* (2013.01); *A61B 3/102* (2013.01); *A61B 5/0066* (2013.01); *G01B 9/02004* (2013.01); *G01B 9/02027* (2013.01); *G01B 9/02075* (2013.01); *G01B 9/02091* (2013.01); *G01B 2290/35* (2013.01); *G01B 2290/70* (2013.01)

(58) Field of Classification Search
CPC ...... G06T 2207/10101; G01B 2290/35; G01B 2290/70; G01B 9/02004; G01B 9/02027; G01B 9/02075; G01B 9/02083; G01B 9/02091; A61B 3/0025; A61B 3/102; A61B 5/0066
See application file for complete search history.

(56) References Cited

U.S. PATENT DOCUMENTS

| | | | |
|---|---|---|---|
| 6,961,123 B1 * | 11/2005 | Wang ........................ | G01J 4/04 356/364 |
| 9,314,160 B2 * | 4/2016 | Adler, Jr. ............. | A61B 5/0033 |

(Continued)

FOREIGN PATENT DOCUMENTS

| | | |
|---|---|---|
| JP | 4344829 B2 | 10/2009 |
| JP | 2013-019773 A | 1/2013 |

OTHER PUBLICATIONS

Makita et al ("Generalized Jones matrix optical coherence tomography: performance and local birefringence imaging", 2010).*

(Continued)

*Primary Examiner* — Avinash Yentrapati
(74) *Attorney, Agent, or Firm* — Shumaker, Loop & Kendrick, LLP

(57) ABSTRACT

The optical coherence tomography includes a processor, wherein the processor is configured to: vectorize the Jones matrix and then convert the vectorized Jones matrix into an expanded matrix; calculate at least an eigenvalue and at least an eigenvector of the expanded matrix by performing an eigenvalue decomposition to the expanded matrix; and estimate the polarization characteristic of the subject by using at least an eigenvalue and at least an eigenvector of the Jones matrix acquired based on the at least eigenvalue and the at least eigenvector of the expanded matrix.

7 Claims, 4 Drawing Sheets

(56) References Cited

U.S. PATENT DOCUMENTS

2009/0180093 A1* 7/2009 Arai .................. G03B 27/54
                                                      355/67
2009/0247862 A1* 10/2009 Meyer ................ A61B 3/102
                                                      600/425
2014/0115022 A1* 4/2014 Yasuno ............. G01B 9/02044
                                                      708/204

OTHER PUBLICATIONS

Shuichi Makita et al.; "Generalized Jones matrix optical coherence tomography: performance and local birefringence imaging"; Optics Express; vol. 18; No. 2, p. 854-876; Jan. 18, 2010. (XP055153680).

* cited by examiner

OPTICAL COHERENCE TOMOGRAPHY USING POLARIZATION INFORMATION

CROSS-REFERENCE TO RELATED APPLICATION

This application claims priority to Japanese Patent Application No. 2015-088041 filed on Apr. 23, 2015, the entire contents of which are hereby incorporated by reference into the present application.

TECHNICAL FIELD

The present disclosure relates to a device which performs optical tomographic imaging by means of optical coherence tomography. In particular, the present disclosure relates to a device which performs optical tomographic imaging including a correction process for improving the accuracy of data measured by polarization-sensitive optical coherence tomography.

DESCRIPTION OF RELATED ART

Optical coherence tomography (OCT), capable of noninvasive and contactless measurement, is widely used as means for acquiring high-resolution tomographic images of body tissues in the field of ophthalmology.

Optical coherence tomography (OCT) is classified into: time domain OCT, called a time domain method, in which tomographic images are acquired while mechanically changing an optical path length of reference light by moving a mirror; spectrum domain OCT, called a Fourier domain method, in which tomographic images are acquired by detecting spectrum information with a spectrometer; and optical frequency sweeping OCT, also called a Fourier domain method, in which tomographic images are acquired by detecting a spectrum interference signal with a wavelength sweeping light source.

Birefringence which changes a polarization state occurs in tissues in which molecules are arranged in a same direction. The retina in the fundus presents a strong birefringence property in the retinal nerve fiber layer, the retinal pigment epithelial layer, the blood vessel wall, the sclera, and the lamina cribrosa. Regarding polarization-sensitive OCT (PS-OCT) which is one type of functional OCT, in order to visualize these tissues by tomographic imaging of the birefringence property, various types of polarization-sensitive OCT have been developed in recent years.

Polarization-sensitive OCT (PS-OCT) is configured to use circularly polarized light or polarization-modulated light as measurement light for observing a sample, and detect interfering light as two orthogonal linearly-polarized light beams.

Japanese Patent No. 4344829 discloses an example of polarization-sensitive OCT (PS-OCT). In this PS-OCT, a polarized beam (beam linearly polarized by a polarizer) from a light source is continuously modulated by using an EO modulator (polarization modulator or electro-optical modulator) simultaneously (synchronously) with B-scan, and the continuously polarization-modulated polarized beam is split into two beams. Then, one of the beams is applied to a sample to obtain the reflected light while the other beam is used as reference light, thereby causing spectral interference of the two beams to perform OCT measurement. Then, of components of this spectral interference, a vertically polarized component and a horizontally polarized component are simultaneously measured using two photodetectors, thereby obtaining a Jones matrix representing the polarization characteristics of the sample.

Meanwhile, Japanese Patent Application Publication No. 2013-019773 discloses a method in which phase difference distribution regarding retardation measured by polarization-sensitive optical coherence tomography is converted into data of symmetrical phase difference distribution by using a distribution conversion function obtained by analyzing the characteristics of noise through Monte Carlo simulation, whereby systematic errors are removed and the true phase value buried in noise is estimated, and thus images obtained by polarization-sensitive optical coherence tomography are corrected more clearly.

As described in Japanese Patent Application Publication No. 2013-019773, by estimating the phase difference distribution regarding the retardation of each element of the Jones matrix acquired by polarization-sensitive OCT, the phase retardation of the Jones matrix is appropriately corrected, thereby realizing favorable quantitative analysis.

In the method disclosed in Japanese Patent Application Publication No. 2013-019773, however, multiple sets of phase difference distribution for different ESNRs, each set being composed of a distribution corresponding to each of multiple phase values from 0 to $\pi$, are created and stored in a storage device, and the true phase value is estimated through Monte Carlo simulation.

That is, an enormous number of distribution sets need to be stored in advance. Since the large data sets have to be referenced at each pixel of OCT data, it requires long processing time. Therefore, the method disclosed in Japanese Patent Application Publication No. 2013-019773 is not practical when applied to diagnostic equipment that cannot have rich processing power.

In order to solve the above-described problems, the present disclosure, focusing on density functions used for quantum mechanics, adopts a novel method in which probability of presence of wave functions in the density function is analogized to probability of appearance of the Jones matrix, thereby providing an optical coherence tomography capable of realizing, in a short time, estimation of polarization characteristics including the phase retardation of the birefringence, and executing favorable quantitative analysis for birefringence of a subject.

BRIEF SUMMARY

In order to achieve the above-described purpose, a polarization-sensitive optical coherence tomography (PS-OCT) disclosed herein is configured to acquire a Jones matrix that expresses a polarization characteristic of a subject, the polarization-sensitive optical coherence tomography comprising a processor, wherein the processor is configured to: vectorize the Jones matrix and then convert the vectorized Jones matrix into an expanded matrix; calculate at least an eigenvalue and at least an eigenvector of the expanded matrix by performing an eigenvalue decomposition to the expanded matrix; and estimate the polarization characteristic of the subject by using at least an eigenvalue and at least an eigenvector of the Jones matrix acquired based on the at least eigenvalue and the at least eigenvector of the expanded matrix.

In order to achieve the above-described purpose, in the optical coherence tomography disclosed herein, the processor may be configured to estimate a phase retardation and/or a diattenuation and/or an optical axis of a birefringence of the subject by using the at least eigenvalue and the at least eigenvector of the Jones matrix acquired based on the at least eigenvalue and the at least eigenvector of the expanded matrix.

In order to achieve the above-described purpose, in the optical coherence tomography disclosed herein, the processor may be configured to vectorize the Jones matrix by using a complete basis set such as a Pauli matrix or a lexicographic order matrix.

In order to achieve the above-described purpose, in the optical coherence tomography disclosed herein, the processor may be configured to expand the vectorized Jones matrix to a 4×4 coherence matrix and/or a 4×4 covariance matrix.

In order to achieve the above-described purpose, in the optical coherence tomography, the processor may be configured to develop the at least eigenvalue of the expanded matrix by diagonalizing the 4×4 coherence matrix and/or the 4×4 covariance matrix.

A correction process according to the present disclosure may be executed based on Cloude-Pottier decomposition. That is, acquired Jones matrix representing the polarization characteristics of the subject may be vectorized by using a complete basis set such as a Pauli matrix or a Lexicographic order matrix, for example. Then, the vectorized Jones matrix may be expanded to, for example, a 4×4 coherence matrix and/or a 4×4 covariance matrix. The expanded 4×4 coherence matrix and/or a 4×4 covariance matrix may be diagonalized and developed to an eigenvalue and an eigenvector. A pseudo probability can be calculated based on the eigenvalue.

Then, expected values of polarization characteristics such as a phase retardation and/or a diattenuation and/or an optical axis of a birefringence of the subject can be estimated by using the calculated pseudo probability and the eigenvector.

In order to achieve the above-described purpose, a polarization-sensitive optical coherence tomography (PS-OCT) disclosed herein is configured to acquire at least a Jones matrix that expresses a polarization characteristic of a subject, the polarization-sensitive optical coherence tomography comprising a processor, wherein the processor is configured to: vectorize the Jones matrix and then convert the vectorized Jones matrix into an expanded matrix; calculate at least an eigenvalue and at least an eigenvector of the expanded matrix by performing an eigenvalue decomposition to the expanded matrix; and calculate a von Neumann entropy that expresses a degree of randomness of the polarization characteristic of the subject by using the eigenvalues of the expanded matrix.

The present disclosure is not limited to the methods according to claims 1 to 5, and a von Neumann entropy may be adopted. For example, the degree of randomness of birefringence that the subject has in a certain space can be calculated by using the von Neumann entropy.

According to the present disclosure, by calculating expected values of a phase retardation and/or a diattenuation and/or a birefringence axis from the Jones matrices acquired by using the above-described innovative method, it is possible to execute favorable quantitative analysis for birefringence of the subject in an extremely short time.

DETAILED DESCRIPTION

[Embodiment]

Figure 1:
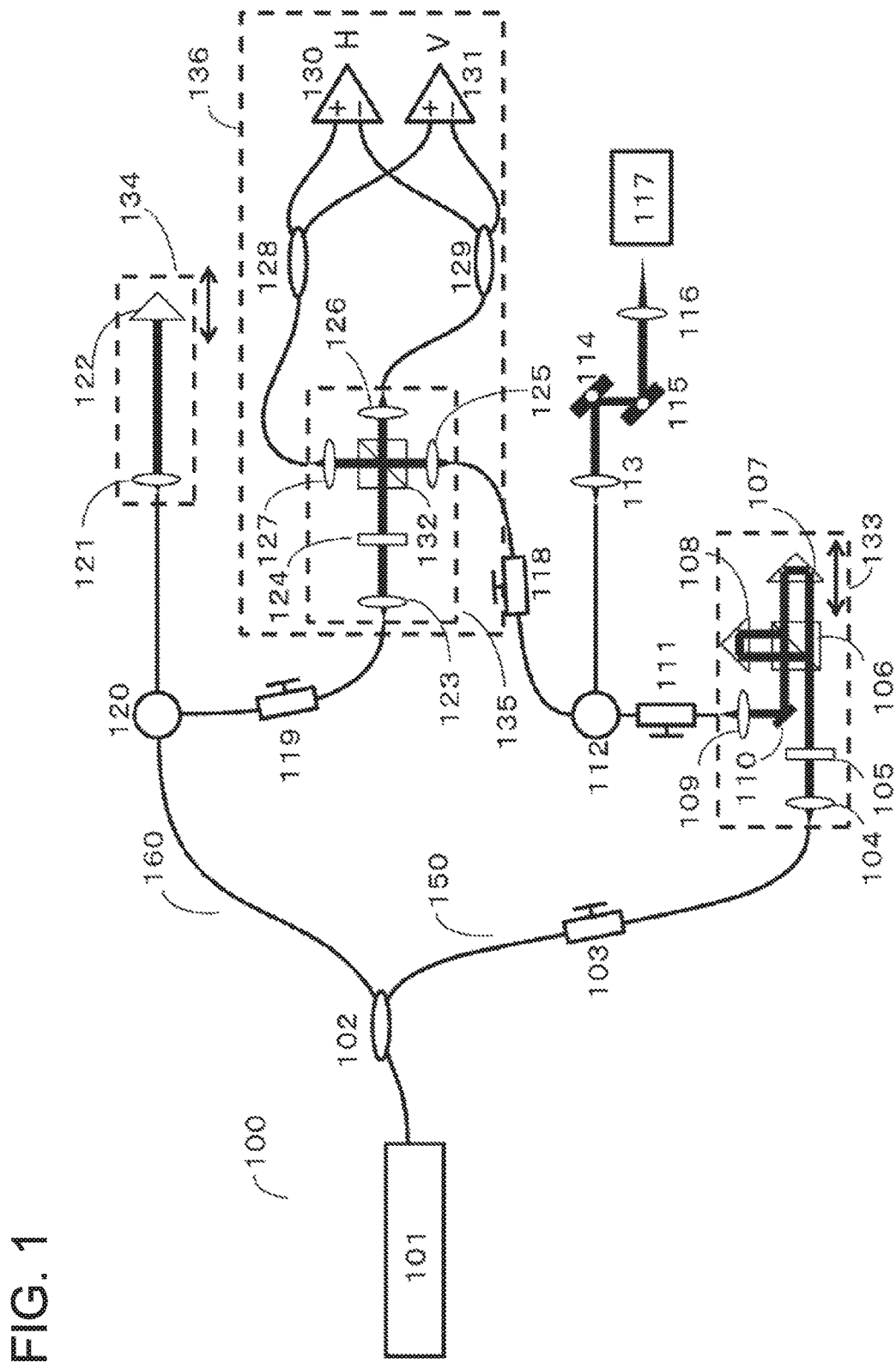
FIG. 1 is a diagram showing an example of an optical tomographic image acquisition section according to a present embodiment in detail.

Hereinafter, an optical tomographic device according to one embodiment of the present disclosure will be described with reference to the drawings. FIG. 1 shows a specific configuration of a tomographic image acquisition section 100.

As shown in FIG. 1, in the tomographic image acquisition section 100, a sample (subject) 117 is irradiated with measurement light to take two-dimensional and/or three-dimensional tomographic image(s) of the sample 117. In the present embodiment, a Fourier domain (optical frequency sweeping) method using a wavelength sweeping light source 101 which allows sweeping with a temporally changing wavelength, is adopted.

That is, light emitted from the wavelength sweeping light source 101 is inputted to a fiber coupler 102 through an optical fiber, and is branched into reference light and measurement light at a ratio of 5:95, for example, in the fiber coupler 102. The reference light and the measurement light are outputted to a reference arm 160 and a sample arm 150, respectively. The reference light outputted to the reference arm 160 is inputted to an optical circulator 120 through the optical fiber and then is inputted to a collimator lens 121, and thereafter is incident on a reference mirror 122. Movement of the reference mirror 122 on an optical axis can be controlled for optical path length adjustment to adjust a reference light path onto a surface position of the sample. In advance of measurement of an OCT tomographic image, a measurement light path length is adjusted to a reference light path length.

Then, the reference light reflected by the reference mirror 122 passes through the collimator lens 121 and the optical fiber. The optical path of the reference light is changed by the optical circulator 120. Then, the reference light passes through a polarization controller 119, is inputted to a collimator lens 123, and then is inputted to a polarization-sensitive detection arm 136.

Meanwhile, the measurement light outputted from the fiber coupler 102 to the sample arm 150 passes through the optical fiber, and is inputted to a collimator lens 104 in a polarization-dependent delay line 133 via a polarization controller 103, and thereafter passes through a polarizer 105. In the present embodiment, the polarization angle of the polarizer 105 is set at 45 degrees. Further, the polarization angle of the measurement light after passing through the polarization controller 103 and immediately before entering the collimator lens 104 is also controlled to be 45 degrees. Thus, in order to efficiently take the measurement light polarized at 45 degrees, the polarization controller 103 and the polarizer 105 are adjusted and controlled.

The measurement light polarized at 45 degrees passes through a polarization beam splitter 106 provided in the polarization-dependent delay line 133, to be split into two light beams in different linear polarization states (vertical direction and horizontal direction) which are orthogonal to each other. The split beams of the measurement light are reflected by different total reflection prisms 107 and 108, and are propagated through two different optical paths, respectively. By controlling movement of at least one of the total reflection prisms 107 and 108, a delay is generated between the two different polarization states (vertical direction and horizontal direction).

By setting the measurement light to be incident on a position a certain distance apart from the center of the polarization beam splitter 106, two beams in different polarization states are generated by the polarization beam splitter 106. The two light beams are reflected by the different total reflection prisms 107 and 108 respectively, whereby two measurement light beams in the different polarization states (vertical direction and horizontal direction) having a certain delay therebetween are generated. Then, the optical paths of the measurement light beams are changed by a reflection mirror 110, and thereafter the light beams are connected to the optical fiber by a collimator lens 109.

The measurement light that has passed through the optical fiber passes through a polarization controller 111. Thereafter, the optical path of the measurement light is changed by an optical circulator 112. Then, the measurement light is incident on a collimator lens 113, is reflected by galvanometer mirrors 114 and 115, and is condensed by a lens 116 to be incident on the sample 117.

The galvanometer mirrors 114 and 115 allow sweeping with the measurement light. A surface of the sample 117 is configured to be scanned with the measurement light in the horizontal direction and the vertical direction by controlling the galvanometer mirrors 114 and 115. Thus, the two-dimensional tomographic image and/or the three-dimensional tomographic image of the sample 117 can be obtained.

The measurement light reflected by the sample 117, reversely to the above route, passes through the lens 116 and the galvanometer mirrors 115 and 114, and is inputted to the collimator lens 113. Then, the measurement light passes through the optical fiber, and the optical path thereof is changed by the optical circulator 112. Thereafter, the measurement light passes through a polarization controller 118, is inputted to a collimator lens 125, and is inputted to the polarization-sensitive detection arm 136.

The reference light which has been outputted from the collimator lens 123 and inputted to the polarization-sensitive detection arm 136 and then polarized by a polarizer 124, and the measurement light reflected by the sample 117 are combined and split again by a non-polarization beam splitter 132. The split light beams are inputted to collimator lenses 126 and 127, respectively, and thereafter are each separated into two mutually orthogonal polarization states by two inline polarization beam splitters 128 and 129, respectively.

In order to equalize the powers of the linearly-polarized beams, in the vertical direction and the horizontal direction, of the reference light after passing through the inline polarization beam splitters 128 and 129, the polarization angle of the polarizer 124 is adjusted to 45 degrees. In addition, in order to efficiently take the reference light, the polarization angle of the reference light immediately before entering the polarizer 124 is controlled to be about 45 degrees by using the polarization controller 119 through which the reference light previously passes.

Figure 2:
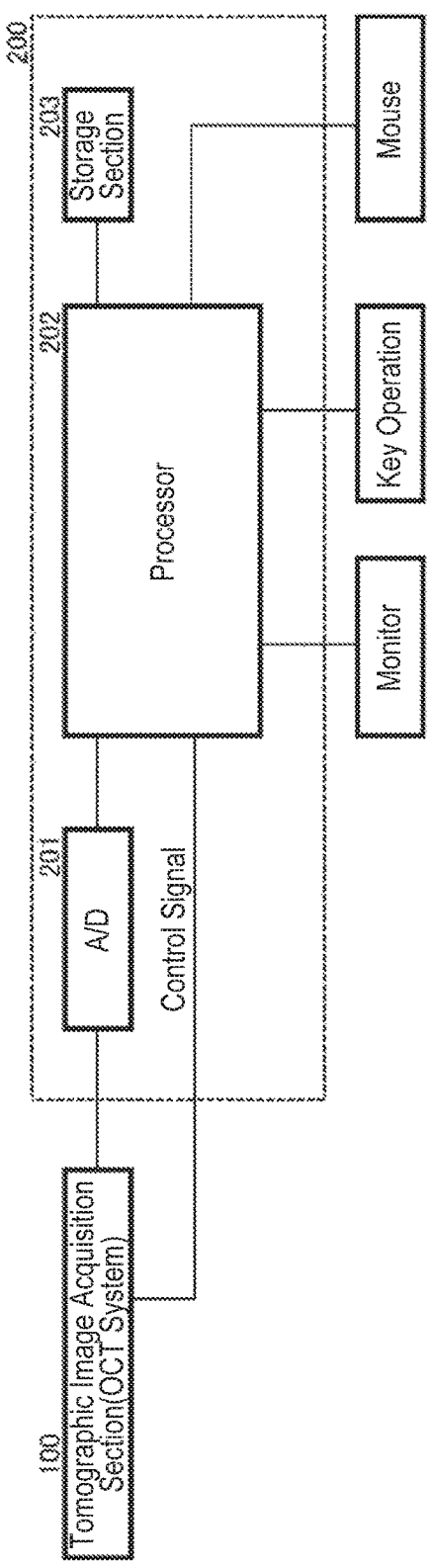
FIG. 2 is a block diagram showing a configuration of an optical tomographic device.

Interference between the two polarization states is detected by two balanced photodetectors 130 and 131. Detected interference signals between the two polarization states in the vertical direction and the horizontal direction are inputted to a processor 202 provided in a control device 200 shown in FIG. 2, and the respective interference signals are subjected to processing such as Fourier transform therein, whereby a B-scan image and/or a C-scan image (volume data) corresponding to a Jones matrix of the sample 117 are acquired. Thus acquired tomographic images are stored in a storage section 203.

Figure 4A:
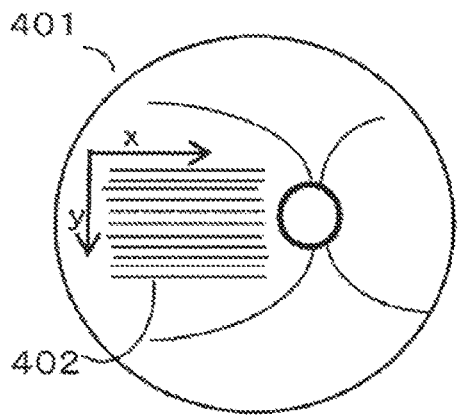
FIGS. 4A, 4B, and 4C are diagrams for explaining a flow of acquiring a three-dimensional tomographic image.
Figure 4B:
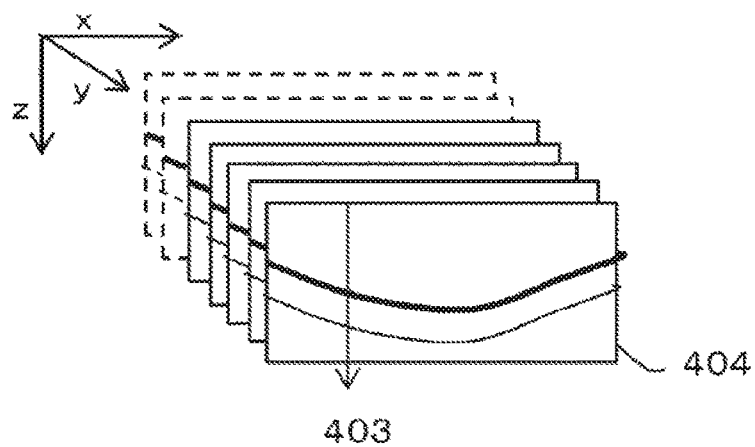
Figure 4C:
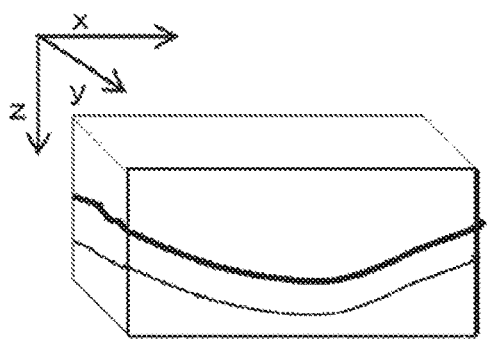

FIGS. 4A to 4C show a manner of acquiring a tomographic image (B-scan image) by the tomographic image acquisition section 100. FIG. 4A shows an example of a fundus retina 401 of a subject's eye 117, and FIG. 4B shows an example of multiple two-dimensional tomographic images (B-scan images) of the fundus retina 401 which are acquired by the tomographic image acquisition section 100. FIG. 4C shows an example of a C-scan image (also referred to as a three-dimensional tomographic image, or volume data) of a fundus portion, which is generated according to the present embodiment. In FIGS. 4A to 4C, an x axis indicates a scanning direction of B-scan, and a y axis indicates a scanning direction of C-scan. Further, in FIGS. 4B and 4C, a z axis indicates a depth direction of an A-scan signal, i.e., a depth direction of the fundus portion.

In FIG. 4B, reference numeral 404 indicates each acquired two-dimensional tomographic image. The two-dimensional tomographic image 404 is formed in such a manner that the processor 202 reconstructs an A-scan signal 403 while the galvanometer mirrors 114 and 115 are caused to perform scanning in the X direction. This two-dimensional tomographic image is a B-scan image, and a two-dimensional tomographic image on a two-dimensional cross section in the X direction orthogonal to the depth direction (Z direction) with respect to the fundus retina 401, i.e., on a plane defined by the x axis and the z axis in FIG. 4B. In FIG. 4A, reference numeral 402 indicates an imaging position of the two-dimensional tomographic image 404.

Figure 3:
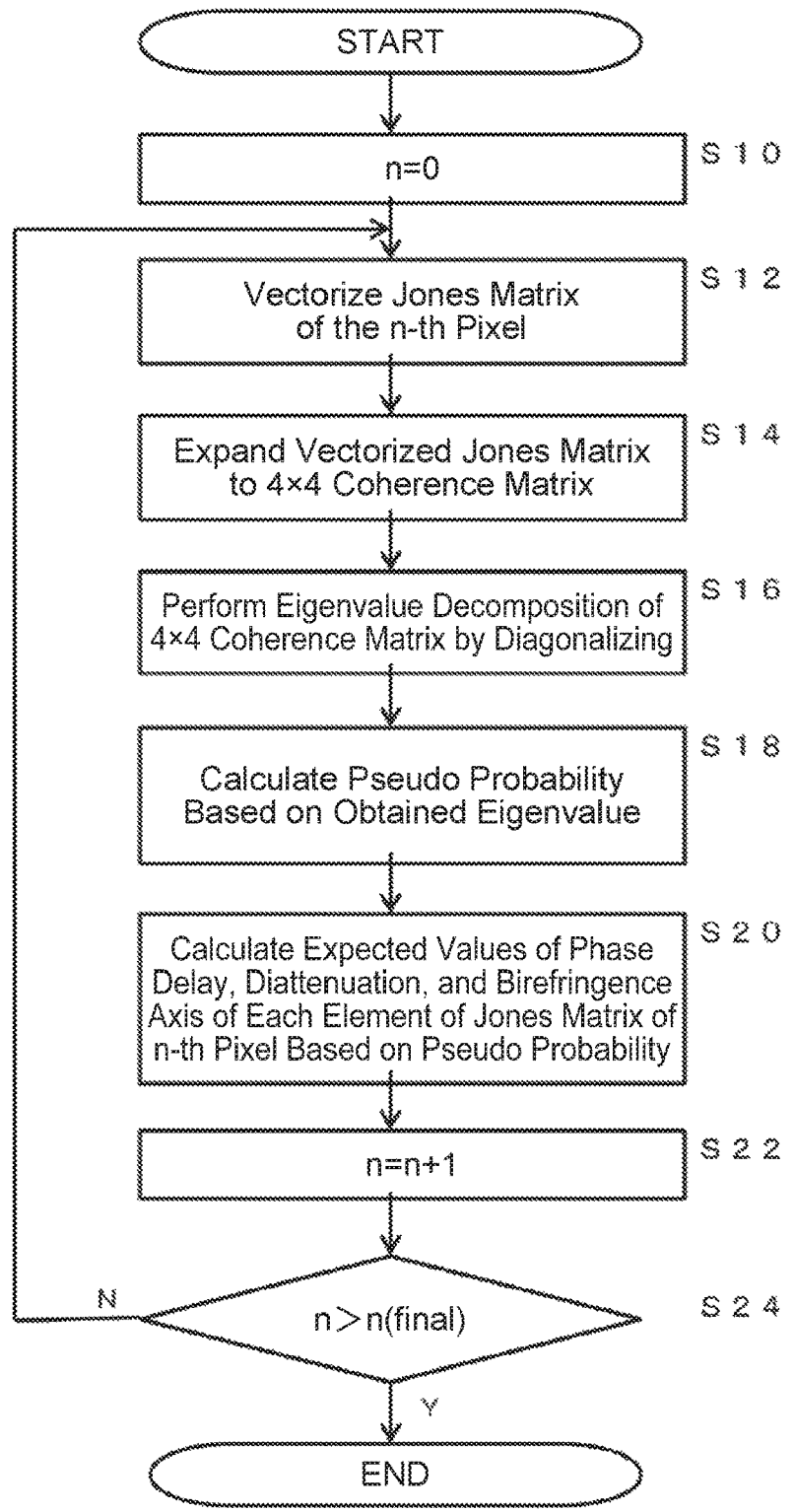
FIG. 3 is a flowchart of a process to calculate expected values based on a pseudo probability according to the present embodiment.

Next, a method for calculating, based on a pseudo probability, an expected value of each element of the Jones matrix of the sample 117, regarding a B-scan image and/or a C-scan image (volume data) acquired according to the Jones matrix, which is a feature of the present disclosure, will be described with reference to a flowchart shown in FIG. 3.

First, a first pixel is set in S10. Since the first pixel is the 0-th pixel, "n=0" is set in S10 so that the set pixel is regarded as the n-th pixel.

Next, in S12, the Jones matrix of the n-th pixel is vectorized.

If the Jones matrix S is defined as:

$$S = \begin{bmatrix} S_{XX} & S_{XY} \\ S_{YX} & S_{YY} \end{bmatrix} \quad \text{[Formula 1]}$$

then a 1×4 target vector k is defined as follows:

$$k = \frac{1}{2} Tr(S\Psi) \quad \text{[Formula 2]}$$

where, Tr( ) represents a matrix trace, and $\Psi$ may be any arbitrary complete basis set. It is noted that the target vector is formed by using all basis sets.

Examples of $\Psi$ include: a Pauli matrix as follows:

$$\{\Psi_P\} = \quad \text{[Formula 3]}$$

$$\left\{ \sqrt{2}\begin{bmatrix} 1 & 0 \\ 0 & 1 \end{bmatrix} \quad \sqrt{2}\begin{bmatrix} 1 & 0 \\ 0 & -1 \end{bmatrix} \quad \sqrt{2}\begin{bmatrix} 0 & 1 \\ 1 & 0 \end{bmatrix} \quad \sqrt{2}\begin{bmatrix} 0 & -j \\ j & 0 \end{bmatrix} \right\}$$

and a Lexicographic order matrix as follows:

$$\{\Psi_L\} = \left\{ 2\begin{bmatrix} 1 & 0 \\ 0 & 0 \end{bmatrix} \ 2\begin{bmatrix} 0 & 1 \\ 0 & 0 \end{bmatrix} \ 2\begin{bmatrix} 0 & 0 \\ 1 & 0 \end{bmatrix} \ 2\begin{bmatrix} 0 & 0 \\ 0 & 1 \end{bmatrix} \right\}$$ [Formula 4]

When the Pauli matrix is used, the target vector is expressed as follows:

$$\underline{k} = \frac{1}{\sqrt{2}}[S_{XX}+S_{YY} \ \ S_{XX}-S_{YY} \ \ S_{XY}+S_{YX} \ \ j(S_{XY}-S_{YX})]^T$$ [Formula 5]

When the Lexicographic order matrix is used, the target vector is expressed as follows:

$$\underline{k} = [S_{XX} \ S_{XY} \ S_{YX} \ S_{YY}]^T$$ [Formula 6]

In S14, the target vector vectorized in S12 is multiplexed by Hermitian conjugate as follows, whereby a 4×4 coherence matrix or a 4×4 covariance matrix is acquired.

$$T = \langle \underline{k} \cdot \underline{k}^\dagger \rangle$$ [Formula 7]

In the present embodiment, the target vector is expanded to a 4×4 coherence matrix T expressed in formula 8, by using the lexicographic order matrix. In formula 8, each ensemble average $\langle \ \rangle$ may be taken spatially or temporally, or may be taken in both space and time.

$$T = \begin{bmatrix} \langle |S_{XX}|^2 \rangle & \langle S_{XX}S_{XY}^* \rangle & \langle S_{XX}S_{YX}^* \rangle & \langle S_{XX}S_{YY}^* \rangle \\ \langle S_{XY}S_{XX}^* \rangle & \langle |S_{XY}|^2 \rangle & \langle S_{XY}S_{YX}^* \rangle & \langle S_{XY}S_{YY}^* \rangle \\ \langle S_{YX}S_{XX}^* \rangle & \langle S_{YX}S_{XY}^* \rangle & \langle |S_{YX}|^2 \rangle & \langle S_{YX}S_{YY}^* \rangle \\ \langle S_{YY}S_{XX}^* \rangle & \langle S_{YY}S_{XY}^* \rangle & \langle S_{YY}S_{YX}^* \rangle & \langle |S_{YY}|^2 \rangle \end{bmatrix}$$ [Formula 8]

In S16, the 4×4 coherence matrix T expanded in S14 is diagonalized and subjected to eigenvalue decomposition. The diagonalized 4×4 coherence matrix T is expressed by the following formula 9:

$$T = U\Lambda U^\dagger$$ [Formula 9]

$$\Lambda = \text{diag}[\lambda_1, \lambda_2, \lambda_3, \lambda_4], \lambda_1 \geq \lambda_2 \geq \lambda_3 \geq \lambda_4$$

where $\Lambda$ is a diagonal matrix having diagonal components $\lambda_1$, $\lambda_2$, $\lambda_3$, and $\lambda_4$, and U is a unitary matrix. U is expressed by using 1×4 eigenvectors $e_1$, $e_2$, $e_3$, and $e_4$ as follows:

$$U = [e_1 \ e_2 \ e_3 \ e_4]$$ [Formula 10]

In S18, a pseudo probability is calculated based on the obtained eigenvalue. The pseudo probability $P_i$ can be calculated as follows based on the eigenvalue of the 4×4 coherence matrix T.

$$P_i = \frac{\lambda_i}{\sum_{k=1}^{4} \lambda_k}, \ i = 1, 2, 3, 4$$ [Formula 11]

Then, in S20, based on the calculated pseudo probability $P_i$, expected values of a phase retardation and/or a diattenuation and/or a birefringence axis are calculated.

Here, the eigenvector $e_i$ of the unitary matrix U is a target vector corresponding to each eigenvalue. Based on the relationship between the target vector and the Jones matrix, the target vector can be uniquely converted to the Jones matrix. For example, when the lexicographic order matrix is used, if each element of the target eigenvector is defined as:

$$e_i = [a_i \ b_i \ c_i \ d_i]^t$$ [Formula 12]

the Jones matrix $L_i$ is calculated as follows:

$$L_i = \begin{bmatrix} a_i & b_i \\ c_i & d_i \end{bmatrix}$$ [Formula 13]

Assuming that the eigenvalues of the Jones matrix $L_i$ are $\varepsilon_1$, $\varepsilon_2$, the phase retardation $R_i$ of each Jones matrix $L_i$ is calculated as follows:

$$R_i = \arg(\varepsilon_1 \varepsilon_2^*)$$ [Formula 14]

where, arg( ) means an argument, and a superscript asterisk represents a complex conjugate.

Then, the diattenuation $D_i$ of each Jones matrix $L_i$ is expressed as follows:

$$D_i = \frac{||\varepsilon_1|^2 - |\varepsilon_2|^2|}{|\varepsilon_1|^2 + |\varepsilon_2|^2}$$ [Formula 15]

Assuming that $v_i$ one of the eigenvectors of the Jones matrix $L_i$, is as follows:

$$v_i = \begin{bmatrix} v_{ix} \\ v_{iy} \end{bmatrix}$$ [Formula 16]

the birefringence axis $s_i$ is calculated as follows:

$$s_i \begin{bmatrix} |v_{ix}|^2 + |v_{iy}|^2 \\ |v_{ix}|^2 - |v_{iy}|^2 \\ 2\text{Re}(v_{ix}v_{iy}^*) \\ -2\text{Im}(v_{ix}v_{iy}^*) \end{bmatrix}$$ [Formula 17]

As described above, the phase retardation and/or the diattenuation and/or the birefringence axis of each Jones matrix $L_i$ are calculated, and the expected values of the phase retardation and/or the diattenuation and/or the birefringence axis can be calculated as follows by using the pseudo probability calculated in S18.

$$\overline{R}_i = \sum_{i=1}^{4} P_i R_i$$ [Formula 18]

$$\overline{D}_i = \sum_{i=1}^{4} P_i D_i$$ [Formula 19]

$$\overline{s}_i = \sum_{i=1}^{4} P_i s_i$$ [Formula 20]

After calculating the expected values of the phase retardation and/or the diattenuation and/or the birefringence axis at the n-th pixel in S20 as described above, "n=n+1" is set in S22, and the processes in S12 to S20 are performed on the next pixel to similarly calculate the expected values of the phase retardation and/or the diattenuation and/or the birefringence axis.

When calculation of the expected values of the phase retardation and/or the diattenuation and/or the birefringence axis has been completed for all the pixels in S24 (n>n (Final)), the series of processes are ended.

As described above, by calculating the expected values of the phase retardation and/or the diattenuation and/or the birefringence axis and using the expected values, the parameters of birefringence are appropriately estimated, thereby realizing favorable quantitative analysis.

The embodiment of the present invention has been described in detail above, but the embodiment is only an example, and the present invention is not to be interpreted in a limited way by the specific description in the embodiment and is implementable with various modifications, revisions, improvements and the like based on the knowledge of those skilled in the art, and any such aspect of implementation is included in the range of the present invention as long as it does not deviate from the spirit thereof.

For example, in the above embodiment, each element of the Jones matrix is appropriately estimated by calculating the expected values based on the pseudo probability. However, alternative method for appropriately estimating the Jones matrix may be adopted, in which a phase retardation $R_1$ calculated from a target eigenvector corresponding to the maximum eigenvalue of the unitary matrix U is set as a representative value of a phase retardation, and representative values of a diattenuation $D_1$ and a birefringence axis $s_1$ are similarly calculated.

Further, a von Neumann entropy expressed as follows may be adopted.

$$H = \sum_{i=1}^{4} -P_i \log_4 P_i \quad [\text{Formula 21}]$$

The von Neumann entropy is used as an index indicating the degree of spatial, or temporal, or spatial and temporal randomness of the polarization characteristic of the subject. The von Neumann entropy allows calculation of the degree of randomness of birefringence that the subject has in a certain space, for example. Thereby, it is possible to evaluate a depolarization effect derived from, for example, the amount of melanin pigment in the retinal pigment epithelium, iris pigment epithelium, and uvea, and evaluate the degree of randomness of birefringence distribution in tissues.

The invention claimed is:

1. A polarization-sensitive optical coherence tomographic device (PS-OCT) configured to acquire a Jones matrix that expresses a polarization characteristic of a subject, the polarization-sensitive optical coherence tomographic device comprising a processor,
wherein the processor is configured to:
vectorize the Jones matrix and then convert the vectorized Jones matrix into an expanded matrix;
calculate at least an eigenvalue and at least an eigenvector of the expanded matrix by performing an eigenvalue decomposition to the expanded matrix; and
estimate the polarization characteristic of the subject by using at least an eigenvalue and at least an eigenvector of the Jones matrix acquired based on the at least eigenvalue and the at least eigenvector of the expanded matrix,
wherein
the processor is configured to estimate at least one of a phase retardation, a diattenuation, and an optic axis of a birefringence of the subject by using the at least eigenvalue and the at least eigenvector of the Jones matrix acquired based on the at least eigenvalue and the at least eigenvector of the expanded matrix, and the processor is configured to vectorize the Jones matrix by using a complete basis set.

2. The optical coherence tomographic device as in claim 1, wherein
the processor is configured to expand the vectorized Jones matrix to at least one of a 4×4 coherence matrix and a 4×4 covariance matrix.

3. The optical coherence tomographic device as in claim 2, wherein
the processor is configured to develop the at least eigenvalue of the expanded matrix by diagonalizing the at least one of the 4×4 coherence matrix and the 4×4 covariance matrix.

4. A polarization-sensitive optical coherence tomography device PS-OCT configured to acquire a Jones matrix that expresses a polarization characteristic of a subject, the polarization-sensitive optical coherence tomography comprising a processor,
wherein the processor is configured to:
vectorize the Jones matrix and then convert the vectorized Jones matrix into an expanded matrix;
calculate at least an eigenvalue and at least an eigenvector of the expanded matrix by performing an eigenvalue decomposition to the expanded matrix; and
estimate the polarization characteristic of the subject by using at least an eigenvalue and at least an eigenvector of the Jones matrix acquired based on the at least eigenvalue and the at least eigenvector of the expanded matrix,
wherein
the processor is configured to vectorize the Jones matrix by using a complete basis set.

5. The optical coherence tomographic device as in claim 4, wherein
the processor is configured to expand the vectorized Jones matrix to at least one of a 4×4 coherence matrix and a 4×4 covariance matrix.

6. The optical coherence tomographic device as in claim 5, wherein
the processor is configured to develop the at least eigenvalue of the expanded matrix by diagonalizing the at least one of the 4×4 coherence matrix and the 4×4 covariance matrix.

7. A polarization-sensitive optical coherence tomographic device (PS-OCT) configured to acquire at least a Jones matrix that expresses a polarization characteristic of a subject, the polarization-sensitive optical coherence tomographic device comprising a processor,
wherein the processor is configured to:
vectorize the Jones matrix and then convert the vectorized Jones matrix into an expanded matrix;
calculate at least an eigenvalue and at least an eigenvector of the expanded matrix by performing an eigenvalue decomposition to the expanded matrix; and calculate a von Neumann entropy that expresses a degree of randomness of the polarization characteristic of the subject by using the eigenvalues of the expanded matrix.

\* \* \* \* \*